US010130802B2

(12) United States Patent
Chae

(10) Patent No.: US 10,130,802 B2
(45) Date of Patent: Nov. 20, 2018

(54) CAPSULE ENDOSCOPE FOR PHOTODYNAMIC AND SONODYNAMIC THERAPY

(71) Applicant: Catholic University Industry Academic Cooperation Foundation, Seoul (KR)

(72) Inventor: Hiun Suk Chae, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 662 days.

(21) Appl. No.: 14/440,097

(22) PCT Filed: Oct. 31, 2013

(86) PCT No.: PCT/KR2013/009793
§ 371 (c)(1),
(2) Date: May 1, 2015

(87) PCT Pub. No.: WO2014/069916
PCT Pub. Date: May 8, 2014

(65) Prior Publication Data
US 2015/0283370 A1    Oct. 8, 2015

(30) Foreign Application Priority Data

Nov. 1, 2012    (KR) .................. 10-2012-0122816

(51) Int. Cl.
*A61M 37/00*    (2006.01)
*A61N 5/00*    (2006.01)
(Continued)

(52) U.S. Cl.
CPC ..... *A61M 37/0092* (2013.01); *A61B 1/00087* (2013.01); *A61B 1/041* (2013.01);
(Continued)

(58) Field of Classification Search
CPC ......... A61B 1/041; A61B 8/12; A61B 8/4472; A61M 37/0092; A61N 5/062; A61N 5/0603; A61N 2007/0043
See application file for complete search history.

(56) References Cited

U.S. PATENT DOCUMENTS

2003/0214579 A1* 11/2003 Iddan ................. A61B 1/00156
348/81
2004/0122315 A1* 6/2004 Krill ...................... A61B 1/041
600/437

(Continued)

FOREIGN PATENT DOCUMENTS

KR    10-2003-0039199    6/2003
KR    10-2008-0127809    12/2008
WO    WO 2011/037299 A1    3/2011

*Primary Examiner* — John P Leubecker
(74) *Attorney, Agent, or Firm* — Hammer & Associates, P.C.

(57) ABSTRACT

A capsule endoscope for photodynamic and sonodynamic therapy is disclosed. The capsule includes: an endoscope body; a light and ultrasonic wave irradiation portion provided on the outer surface of the endoscope body and irradiating light of different wavelengths and ultrasonic waves; and a photodynamic and sonodynamic therapy portion connected to the outer surface of the endoscope body and comprising a material for photodynamic and sonodynamic therapy, wherein the photodynamic and sonodynamic therapy portion can be activated by the light and ultrasonic waves irradiated from the light and ultrasonic wave irradiation portion. The capsule endoscope can treat local bacterial infection, or diabetes, malignant diseases, chronic colitis and the like caused by a change in the number and type of intestinal floras while passing through the body in addition to carrying out diagnosis, which is the inherent function of a capsule endoscope, and thus there is no need for additional treatment and a patient can comfortably receive therapy.

5 Claims, 2 Drawing Sheets

(51) Int. Cl.
*A61N 7/00* (2006.01)
*A61B 1/00* (2006.01)
*A61B 1/04* (2006.01)
*A61N 5/06* (2006.01)

(52) U.S. Cl.
CPC ........... *A61N 5/0601* (2013.01); *A61N 5/062* (2013.01); *A61N 7/00* (2013.01); *A61N 5/0603* (2013.01); *A61N 2007/0043* (2013.01)

(56) References Cited

U.S. PATENT DOCUMENTS

| | | | |
|---|---|---|---|
| 2004/0171601 A1* | 9/2004 | Fukumura | A61K 31/555 514/185 |
| 2004/0249245 A1 | 12/2004 | Irion | |
| 2005/0192478 A1 | 9/2005 | Williams et al. | |
| 2007/0142708 A1* | 6/2007 | Yokoi | A61B 1/00016 600/118 |
| 2007/0264732 A1* | 11/2007 | Chen | A61B 1/041 438/22 |
| 2009/0036952 A1* | 2/2009 | Kao | A61N 5/062 607/88 |
| 2009/0306633 A1* | 12/2009 | Trovato | A61B 1/041 604/891.1 |
| 2010/0047356 A1 | 2/2010 | Yu et al. | |
| 2010/0217079 A1* | 8/2010 | Tichy | A61B 1/00147 600/118 |
| 2011/0201993 A1* | 8/2011 | Takei | A61B 1/041 604/20 |
| 2012/0184850 A1* | 7/2012 | Gutierrez | A61N 5/0603 600/439 |
| 2012/0253200 A1* | 10/2012 | Stolka | A61B 1/041 600/459 |
| 2014/0081360 A1* | 3/2014 | Ben-Yehuda | A61N 5/0603 607/92 |

* cited by examiner

CAPSULE ENDOSCOPE FOR PHOTODYNAMIC AND SONODYNAMIC THERAPY

TECHNICAL FIELD

The present invention relates to a capsule endoscope. More particularly, the present invention relates to a capsule endoscope for photodynamic and sonodynamic therapy that is inserted into a human body and can be used for not only diagnosis, but medical treatment by diagnosing local bacterial infection, small and large intestinal diseases, chronic inflammatory intestinal diseases such as ulcerative colitis or a crohn's disease, and digestive malignant diseases, or by activating a photosensitizer with light and ultrasonic waves having a specific wavelength to treat or prevent diseases by adjusting the types or number of intestinal bacteria.

BACKGROUND ART

Antibiotics have been used against various pathogens including bacteria. However, more people have been recently died for infection with pathogens such as various bacteria (so-called super bacteria) being tolerant to various antibiotics that are used at present.

For example, the death rate of people with *clostridium difficile* infection (CDI), one of digestive infection, due to bacteria tolerant to metronidazole and vancomycin, which are antibiotics have been used from the past, has been increasing, and it has become an issue usually in developed countries, but there have been some cases even in our country. The patient compliance is another problem in treatment with antibiotics against infectious diseases and there are some cases that patients cannot take an antibiotic or are allergic to an antibiotic. Accordingly, there is a need for developing a treatment capable of replace antibiotics to treat diseases due to pathogens.

Further, considering the fact, which has been found in recent years, that metabolites produced by a change in the types and number of intestinal floras is associated with the reasons for diseases such as diabetes, malignant diseases, and chronic colitis, there is a need for developing a treatment for adjusting the types or number of intestinal bacteria.

Meanwhile, the PDT (Photodynamic therapy) and SDT (Sonodynamic therapy) using light and ultrasonic waves, which are treatments used against malignant tumors or local bacterial infection, treat pathogens using photosensitizers (PS) having specific wavelengths, in which reactive oxygen species (ROS) are produced by the action of light or ultrasonic waves and PS and damage cell walls, cell membranes, or nucleic acid, thereby achieving germicidal and antitumor effect.

The photosensitizer is largely divided into two types of a porphyrin PS and a non-porphyrin PS. This treatment is generally used for treatments against spatially limited infection, including dermatologic or dental treatment. Pathogens that live and propagate in clusters in human bodies are little influenced by light and ultrasonic waves, so their genes against a hurt due to light and ultrasonic waves have degenerated and almost disappeared and there has not been found a gene tolerant to this treatment.

Accordingly, the photodynamic and sonodynamic therapies against the pathogens in a human body are expected to have considerably effect and can save costs and suppress bacteria tolerant to antibiotics by reducing use of antibiotics. Further, since a PDT or an SDT is used first before administration of an antibiotic, so they can reduce at least bacterial loading and can reduce the death rate due to bacterial infection with an economic effect by being used with antibiotics.

In general, capsule endoscopes that are inserted into a human body have been used only for diagnosis. Such capsule endoscopes have been disclosed in Korean Patent Application Publication Nos. 2004-0108277 and 2010-0069192.

Therefore, the applicant(s) proposes a capsule endoscope that can be used not only for diagnosis, but for a treatment of local bacterial infection, small and large intestinal diseases, chronic inflammatory intestinal diseases such as ulcerative colitis or a crohn's disease, diabetes, and digestive malignant diseases, through a photodynamic and sonodynamic therapy.

DISCLOSURE

Technical Problem

Accordingly, an object of the present invention is to provide a capsule endoscope for a photodynamic and sonodynamic therapy that can perform a photodynamic and sonodynamic therapy by being inserted into intestines and activating a photosensitizer with light and ultrasonic waves with specific wavelengths, for example, to treat various types of diseases including enteritis.

The technical subjects to implement in the present invention are not limited to the technical problems described above and other technical subjects that are not stated herein will be clearly understood by those skilled in the art from the following specifications.

Technical Solution

In order to achieve the object, the present invention provides a capsule endoscope for a photodynamic and sonodynamic therapy that includes: an endoscope body; light/ultrasonic wave radiators disposed surrounding the surface of the endoscope body and radiating light/ultrasonic waves with different wavelengths; and photodynamic/sonodynamic treaters connected to the surface of the endoscope body and including substances for a photodynamic/sonodynamic therapy, in which the photodynamic/sonodynamic treaters are activated by light and ultrasonic waves from the light/ultrasonic wave radiators.

The photodynamic/sonodynamic treaters may be connected to the endoscope body by connecting fibers that are decomposed at a pH condition in an intestine.

The light/ultrasonic wave radiators may be disposed like bands surrounding the surface of the endoscope body.

The endoscope body may have the shape of a cylinder or a rugby ball.

The photodynamic/sonodynamic treaters may have the shape of a microcapsule and multiple substances for the photodynamic/sonodynamic therapy may be at least one selected from a group consisting of a light or ultrasonic sensitizer, an antibiotic, a nano-substance, and probiotics.

Cameras may be disposed at the front and the rear of the endoscope body.

The light/ultrasonic wave radiators and the cameras may be controlled to be turned on/off from the outside of a human body.

Further, the present invention provides a method of treating local bacterial infection, chronic inflammatory intestinal diseases, diabetes, or digestive malignant diseases, comprising: administrating the capsule endoscope for photodynamic and sonodynamic therapy into a patient; and radiating light and ultrasonic waves.

The chronic inflammatory intestinal diseases may be related with composition of harboring local bacteria, small and large intestinal diseases, ulcerative colitis, or a crohn's disease.

Advantageous Effects

The present invention provides a capsule endoscope for photodynamic and sonodynamic therapy that achieves an antibacterial effect using ROS, by means of activating photosensitizers that are separated by connecting fibers decomposed by light and ultrasonic waves having a specific wavelength radiated to the capsule endoscope in a human body.

Therefore, according to the present invention, the capsule endoscope can perform diagnosis, which is the basic function of capsule endoscopes, and also treat diseases such as local bacterial infection, diabetes, malignant diseases, and chronic colitis due to a change in the types and number of intestinal floras. Therefore, there is no need for a specific therapy and a patient can be comfortably treated.

BEST MODE

An embodiment of a capsule endoscope for a photodynamic and sonodynamic therapy according to the present invention will be described hereafter in detail with reference to the accompanying drawings.

Figure 1:
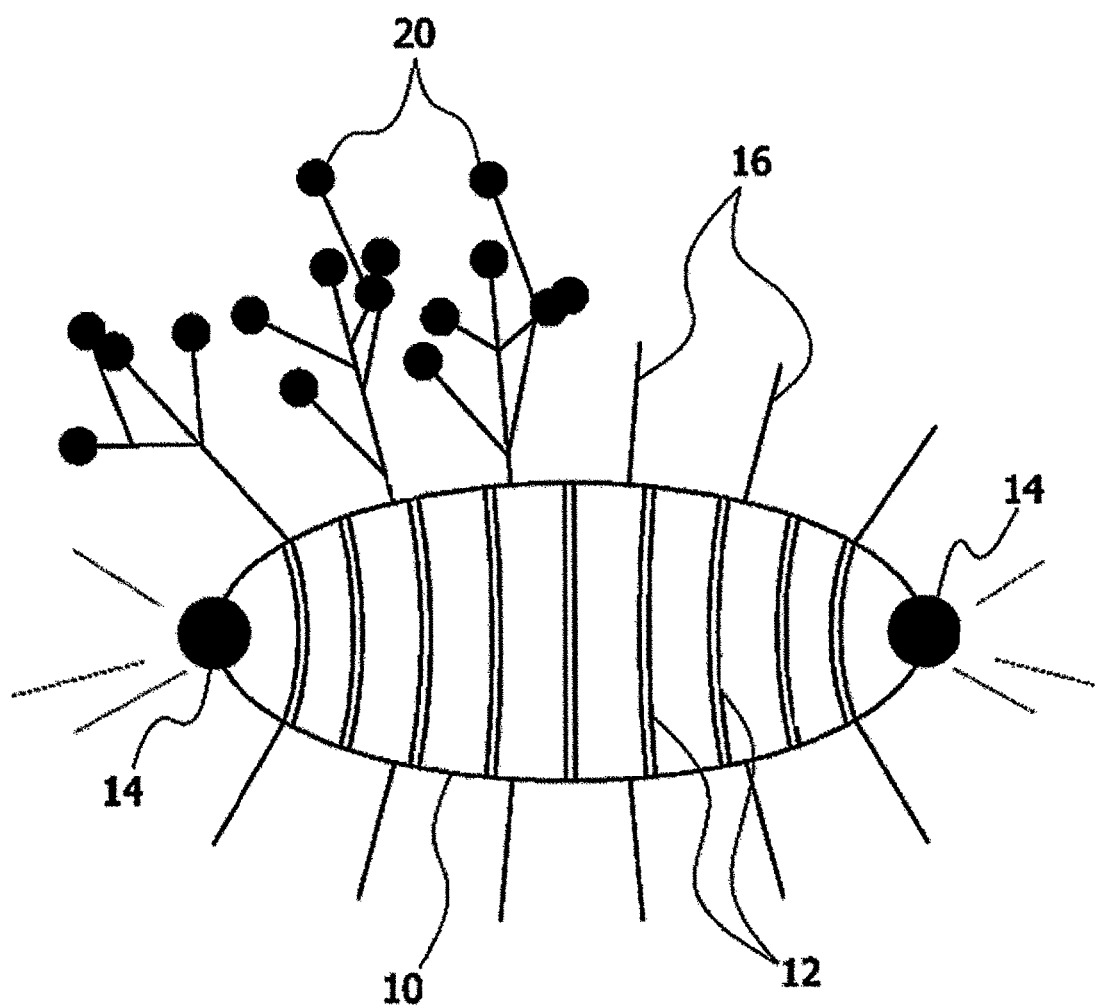
FIG. 1 is a view illustrating the configuration of a capsule endoscope for a photodynamic and sonodynamic therapy according to an embodiment of the present invention.

FIG. 1 is a view illustrating the configuration of a capsule endoscope for a photodynamic and sonodynamic therapy according to an embodiment of the present invention.

Referring to FIG. 1, a capsule endoscope for a photodynamic and sonodynamic therapy according to the present invention includes: an endoscope body 10; light and ultrasonic wave radiators 12 disposed surrounding the surface of the endoscope body 10 and radiating light and ultrasonic waves with different wavelengths; and photodynamic and sonodynamic treaters 20 connected to the surface of the endoscope body 10 and containing substances for a photodynamic and sonodynamic therapy.

The endoscope body 10 is a rugby ball-shaped capsule, as illustrated in FIG. 1. Obviously, the endoscope body 10 may be formed in other various shapes, such as a cylinder and a rectangle, instead of the shape illustrated in FIG. 1. That is, the endoscope body 10 may be formed in any shape, as long as it can be inserted into a human body.

The plurality of light and ultrasonic wave radiators 12, which are disposed around the surface of the endoscope body 10, may be arranged around the surface of the endoscope body 10 in various shapes, like bands, and at various angles. The light and ultrasonic wave radiators 12 radiate light and ultrasonic waves with different wavelengths. The light and ultrasonic waves from the radiators 12 provide a photodynamic and sonodynamic effect for treating bacteria in a human body by activating a photosensitizer. The different wavelengths generated by the radiators 12 are provided to treat various pathogens by activating various photosensitizers.

Further, the light and ultrasonic wave radiators 12 can be controlled to radiate light and ultrasonic waves or by a controller (not illustrated) outside a human body. For example, the controller observes the inside of a human body through cameras 14 to be described below and transmits a signal to the light and ultrasonic wave radiators 12 so that they radiate light and ultrasonic waves with a wavelength fitting to bacteria at a portion to be treated. Accordingly, it is possible to selectively treat various pathogens, observing the inside a human body outside in real time, after inserting the capsule endoscope into the human body.

Meanwhile, the cameras 14 are disposed at the front and the rear of the endoscope body 10. The cameras 14 take pictures of mucous membranes in a human body, similar to those on general capsule endoscopes. Although the cameras 14 are disposed at the front and the rear of the endoscope body 10 in FIG. 1, they are not necessarily limited thereto and may be disposed at various portions such as the side of the endoscope body 10. Further, the cameras 14 can be controlled to be turned on/off by the controller outside a human body, equal to the light and ultrasonic wave radiators 12.

Further, a plurality of connecting fibers 16 is disposed on the surface of the endoscope body 10. The connecting fibers 16 function as media connecting the photodynamic and sonodynamic treaters 20 to the endoscope body 10 and may be elastically disposed on the surface of the endoscope body 10 like villi. In the embodiment, the connecting fibers 16 may be decomposed by only a specific condition (specific PH or specific enzymes secreted from bacteria or tissues). This is for completely separating the connecting fibers 16 and sending to a desired portion by decomposing them from the photodynamic and sonodynamic treaters 20. For example, the connecting fiber 16 may be decomposed at a specific PH, particularly, in a large intestine. Further, the connecting fibers 16 may be decomposed by various substances secreted from bacteria and tissues of a human.

Meanwhile, the photodynamic and sonodynamic treaters 20 have the shape of a microcapsule and may contain one or more selected from a group of a light or ultrasonic sensitizer, an antibiotic, a nano-substance, and probiotics, as a substance for the photodynamic and sonodynamic therapy. The photodynamic and sonodynamic treaters 20, as described above, are separated from the endoscope body 10 and sent to a desired portion with decomposition of the connecting fibers 16 and the photo sensitizer is activated by light and ultrasonic waves from the light and ultrasonic wave radiators 12, so ROS generate antibacterial activity. Microcapsules are also decomposed by specific conditions in an intestine (for example, enteritis or *helicobacter pylori* infection of a stomach) and the contents described above leak out.

Figure 2:
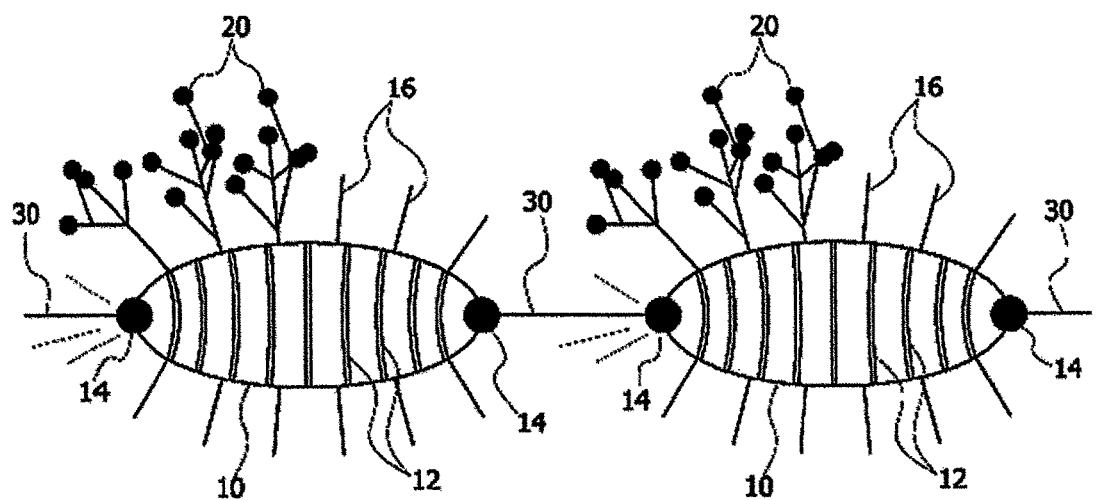
FIG. 2 is a view illustrating a connection configuration of a plurality of capsule endoscopes for a photodynamic and sonodynamic therapy according to an embodiment of the present invention.

Next, FIG. 2 is a view illustrating a connection configuration of a plurality of capsule endoscopes for a photodynamic and sonodynamic therapy according to an embodiment of the present invention.

Referring to FIG. 2, a plurality of the capsule endoscope for a photodynamic and sonodynamic therapy illustrated in FIG. 1 can be connected by a connector 30, as in FIG. 2. Such a combination is for profoundly potentiating the antibacterial effect by one capsule endoscope and an appropriate number of the capsule endoscopes can be connected and inserted into the body of a patient, depending on the patient's condition.

The capsule endoscope for a photodynamic and sonodynamic therapy described above may be designed to act usually an intestine. Food poisoning by bacteria or enteritis by bacterial infection, particularly, CDI (*clostridium difficile* infection), which is associated with an intestine, does not react to a treatment due to tolerance to antibiotics, so deaths increases and large personal and economic losses is caused by reccurrence, but there has been little attempt up to now to perform photodynamic and sonodynamic therapy against various bacterial enteritis including CDI.

Therefore, in the embodiment, the capsule endoscope for a photodynamic and sonodynamic therapy has been designed to be able to perform a photodynamic and sonodynamic therapy, with the connecting fibers 16 decomposed by PH, enzymes secreted by bacteria, and substances secreted due to inflammation in a human body, particularly, when it passes through an intestine. Obviously, the capsule endoscope for a photodynamic and sonodynamic therapy may be designed to perform a photodynamic and sonodynamic therapy in other internal organs in accordance with conditions of them.

The present invention is not limited to the exemplary embodiments described above and defined by claims, and it is apparent to those skilled in the art that the present invention may be modified in various ways without departing from the scope of the present invention described in claims.

The invention claimed is:

1. A capsule endoscope for a photodynamic and sonodynamic therapy, comprising:
    an endoscope body;
    a plurality of light and ultrasonic wave radiators disposed in a form of bands surrounding a surface of the endoscope body, wherein each of the light and ultrasonic wave radiators radiate light and ultrasonic waves with different wavelengths; and
    a plurality of photodynamic and sonodynamic treaters connected to the surface of the endoscope body and containing substances for a photodynamic and sonodynamic therapy,
    wherein the substances are activated by light and ultrasonic waves from the light and ultrasonic wave radiators,
    wherein the photodynamic and sonodynamic treaters are connected to the endoscope body by connecting fibers that are decomposed at a pH condition in an intestine.

2. The capsule endoscope of claim 1, wherein the endoscope body has the shape of a cylinder or a rugby ball.

3. The capsule endoscope of claim 1, wherein the photodynamic and sonodynamic treaters have the shape of multiple microcapsules and the substances for the photodynamic and sonodynamic therapy is at least one selected from a group consisting of a light or ultrasonic sensitizer, an antibiotic, a nano-substance, and probiotics.

4. The capsule endoscope of claim 1, wherein cameras are disposed at a front and a rear of the endoscope body.

5. A capsule endoscope for photodynamic and sonodynamic therapy, comprising:
    a plurality of capsule endoscopes of claim 1; and
    connectors that connect the plurality of capsule endoscopes.

* * * * *